United States Patent [19]

Machinami et al.

[11] Patent Number: 5,171,746
[45] Date of Patent: Dec. 15, 1992

[54] THIAZOLE AND IMIDAZOLE DERIVATIVES AND ANTIULCER COMPOSITION CONTAINING SAME

[75] Inventors: Tomoya Machinami; Kazue Yasufuku; Seiji Shibahara; Yasukatsu Yuda; Fumiya Hirano, all of Yokohama, Japan

[73] Assignee: Meiji Seika Kabushiki Kaisha, Tokyo, Japan

[21] Appl. No.: 683,176

[22] Filed: Apr. 9, 1991

[30] Foreign Application Priority Data

Apr. 9, 1990 [JP] Japan .................. 2-92280
Apr. 9, 1990 [JP] Japan .................. 2-93452
Apr. 9, 1990 [JP] Japan .................. 2-93453

[51] Int. Cl.$^5$ .............. A61K 31/425; C07D 277/74; C07D 277/76
[52] U.S. Cl. .................. 514/367; 548/166; 548/169; 548/171; 548/173; 548/174
[58] Field of Search ............. 548/171, 166, 169, 173, 548/174; 514/367

[56] References Cited

U.S. PATENT DOCUMENTS 2,410,407  11/1946  Dusland ................. 548/157
4,451,471   5/1984  Ferrini et al. .......... 548/194
4,567,267   1/1986  Wei et al. ............. 548/171

OTHER PUBLICATIONS

D'Amico, J. Heterocyclic Chem. 24, pp. 945-948 (1987).
Sanfilippo et al., J. Med. Chem. 31, pp. 1778-1785 (1988).

*Primary Examiner*—Joseph Paul Brust
*Assistant Examiner*—MarySusan H. Gabilan
*Attorney, Agent, or Firm*—Wenderoth, Lind & Ponack

[57] ABSTRACT

A thiazole or imidazole derivative having the general formula (I):

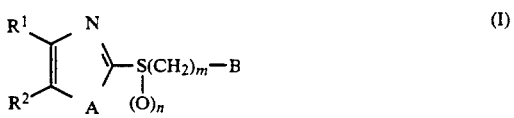

wherein:

$R^1$ and $R^2$, which may be the same or different, each independently represent a hydrogen atom, or a phenyl or heteroaryl group, or $R^1$ and $R^2$ may together form a benzene ring which may be optionally substituted by a halogen atom or a lower alkyl optionally substituted by a halogen atom, lower alkoxy or nitro group;

A represents a sulfur atom or —NH—;

B represents a lower alkoxy group optionally substituted by a halogen atom; a five- or six-membered saturated heterocyclic ring containing one nitrogen or oxygen atom which ring may be optionally substituted; a six-membered saturated heterocyclic ring containing one oxygen atom plus one nitrogen atom; a group —$XR^3$ where X represents a group —$NR^4$ wherein $R^3$ and $R^4$, which may be the same or different, each independently represent a lower alkyl group; or a group —$NHC(=Y)R^5$ where Y represents an oxygen or sulfur atom or a group =NCN or =CHNO$_2$, and $R^5$ represents a group —$NHR^6$ or —$SR^6$ wherein $R^6$ represents a lower alkyl group optionally substituted by a halogen atom;

m is an integer from 1 to 4; and
n is an integer from 0 to 2;

and their pharmacologically acceptable salts. The compounds have an antiulcerative activity.

7 Claims, No Drawings

THIAZOLE AND IMIDAZOLE DERIVATIVES AND ANTIULCER COMPOSITION CONTAINING SAME

BACKGROUND OF THE INVENTION

1. Field of the Invention

The present invention relates to thiazole or imidazole derivatives having an antiulcer activity. This invention also concerns an antiulcer composition efficacious for treating and preventing gastric and duodenal ulcers, which contains them as an effective ingredient.

2. Description of the Related Art $H_2$-receptor antagonists represented by "Cimetidine" and muscarine receptor blockers such as "Pirenzepine" have been used as antiulcer agents. In addition, the development of "Omeprazole" and "NC-1300" based on benzimidazole derivatives that are $H^+/K^+$-ATPase inhibitors possessing new mechanisms is now in the making.

It has been reported that some benzothiazole derivatives possess an inhibitory action on $H^+/K^+$-ATPase ("J. Med. Chem.", 1983, 31, pp. 1778–1785).

We have filed patent applications relating to some relevant techniques (Japanese Patent Application Nos. 293689/1988 and 320468/1988).

Some 2-thio, 2-sulfinyl or 2-sulfonyl-thiazole derivatives have been known with their synthetic processes (e.g. European Patent No. 61425 specification). However, these compounds are described as an antirheumatic agent. Never until now have they been reported to have an antiulcer action.

Some benzothiazole derivatives containing a thiolcarbamoyl group have been known and synthesized by conventional processes so far available in the art (e.g. "J. Heterocycl. Chem.", 24(4), pp. 945-8). This is also true of some benzothiazole derivatives containing an urea group (U.S. Pat. No. 2,410,407). However, these are different from the compounds of this invention represented by Formula (I), in terms of the group "B". Never until now have they been reported to possess an antiulcer action.

SUMMARY OF THE INVENTION

It is therefore a primary object of this invention to provide a novel version of thiazole or imidazole derivative having an improved antiulcer activity.

In order to achieve this object and in search of valuable antiulcer agents, we have synthesized a variety of compounds, and have now found that some thiazole or imidazole derivatives are efficacious against ulcers.

Thus, the present invention concerns a novel compound. The compound according to this invention is a novel thiazole or imidazole derivative having the general formula (I):

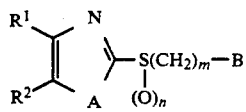
(I)

wherein:

$R^1$ and $R^2$, which may be the same or different, each independently represent a hydrogen atom, or a phenyl or heteroaryl group, or $R^1$ and $R^2$ may together form a benzene ring which may be optionally substituted by a halogen atom or a lower alkyl optionally substituted by a halogen atom, lower alkoxy or nitro group;

A represents a sulfur atom or —NH—;

B represents a lower alkoxy group optionally substituted by a halogen atom; a five- or six-membered saturated heterocyclic ring containing one nitrogen or oxygen atom which ring may be optionally substituted; a six-membered saturated heterocyclic ring containing one oxygen atom plus one nitrogen atom; a group —$XR^3$ where X represents a group —$NR^4$ wherein $R^3$ and $R^4$, which may be the same or different, each independently represent a lower alkyl group; or a group —NHC(=Y)$R^5$ where Y represents an oxygen or sulfur atom or a group =NCN or =$CHNO_2$, and $R^5$ represents a group —$NHR^6$ or —$SR^6$ wherein $R^6$ represents a lower alkyl group optionally substituted by a halogen atom;

m represents an integer from 1 to 4; and n represents an integer from 0 to 2;

and their pharmacologically acceptable salts.

The present invention is also directed to the use of such a novel compound. Compounds of formula (I), which have an antiulcer activity, are useful in the treatment of ulcer condition. Accordingly, the present invention provides a pharmaceutical composition which comprises at least one compound selected from compounds of the general formula (I) and their pharmaceutically acceptable salt.

DETAILED DESCRIPTION OF THE INVENTION

Compounds

The compounds according to the present invention are represented by the above-mentioned formula (I).

The alkyl group moiety of the lower alkyl or alkoxy group may preferably mean a straight or branched $C_{1-4}$ alkyl group.

In the compounds of formula (I), $R^1$ and $R^2$, which may be the same or different, each independently represent a hydrogen atom or a phenyl or heteroaryl group. The term "heteroaryl group" means preferably a five- or six-membered heterocyclic aromatic ring containing at least one hetero-atom selected from the group consisting of nitrogen, oxygen and sulfur atoms, for example, a pyridyl group, a five- or six-membered heterocyclic aromatic ring containing one oxygen or nitrogen atom, for example, thienyl and furanyl group, and a five- or six-membered heterocyclic aromatic ring containing one oxygen atom or one sulfur atom plus one nitrogen atom, for example, a thiazolyl group.

$R^1$ and $R^2$ together may also form a benzene ring which may be optionally substituted by halogen atoms, lower alkyl, halogen-substituted lower alkyl, lower alkoxy and nitro groups.

Representative examples of the five- or six-membered saturated heterocyclic ring represented by B may include pyrrolidinyl, piperidino, piperidyl, tetrahydrofuranyl and tetrahydropyranyl groups in which one or more hydrogen atoms have been substituted by, for example, lower alkyl groups. Representative examples of the six-membered saturated heterocyclic rings represented by B may include morpholino and morpholinyl groups.

A preferred class of compounds of general formula (I) is that wherein $R^1$ and $R^2$ each independently represent a hydrogen atom or a phenyl or heteroaryl group, A is a sulfur atom and B is the group —$XR^3$.

Another preferred class of compounds of general formula (I) is that wherein $R^1$ and $R^2$ together form a benzene ring, A is a sulfur or oxygen atom, and B is a lower alkoxy group, a five- or six-membered saturated heterocyclic ring containing one nitrogen or oxygen atom which ring may be optionally substituted, or a six-membered heterocyclic ring containing one oxygen atom and one nitrogen atom. In this class of compounds, the benzene ring formed by the combination of $R^1$ with $R^2$ may be substituted by a halogen atom or a lower alkyl optionally substituted by a halogen atom, lower alkoxy or nitro group.

A further preferred class of compounds of general formula (I) is that wherein $R^1$ and $R^2$ together form a benzene ring, A is a sulfur atom and B is the group—$NHC(=Y)R^5$. In this class of compounds, the benzene ring formed by the combination of $R^1$ with $R^2$ may be substituted by halogen atoms.

The compounds of formula (I) may exist in the form of their salts.

With the use of salts in mind, pharmaceutically acceptable salts are preferred. Suitable pharmaceutically acceptable salts of the compounds of formula (I) include acid salts such as hydrochlorides, hydrobromides, acetates, succinates and lactates; basic salts with suitable bases such as sodium, potassium, calcium, ammonium, triethylamine and ethanolamine; and amino acid salts with a suitable amino acid such as lysine, arginine and aspartic acid.

It will be appreciated that the compounds of formula (I) have an asymmetric carbon atom, and all optical and geometric isomers of compounds of formula (I) are embraced by the invention.

Preparation of Compounds

Compounds of general formula (I) according to the present invention may be synthesized by any processes as described below.

The compounds of general formula (I) wherein n=0 having the general formula (Ia):

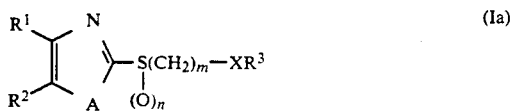

(wherein A, $R^1$, $R^2$, $R^3$, X and m are as defined in general formula (I)) may be obtained by the following process (i) or (ii).

Process (i)

Compounds of formula (Ia) may be prepared by reaction of a compound having the general formula (II):

(wherein $R^1$ and $R^2$ are as defined in general formula (I)) with a compound having the general formula (III):

$$Z^1(CH_2)_m—B^1 \quad (III)$$

(wherein m is as defined in general formula (I), $B^1$ represents a lower alkoxy group optionally substituted by a halogen atom, a five- or six-membered saturated heterocyclic ring containing one nitrogen or oxygen atom which ring may be optionally substituted, a six-membered saturated heterocyclic ring containing one oxygen atom plus one nitrogen atom, or a group —$XR^3$ in which $R^3$ is as defined in general formula (I), and $Z^1$ is a halogen atom or an acyloxy or sulfonyloxy group) in the presence of a hydrogenated metal, preferably hydrogenated sodium or sodium hydroxide, and in an inert solvent, e.g. N,N-dimethylformamide.

It is understood that the synthesis of Compound (II) may be carried out according to known procedures (see "Aus. J. Chem.", 33, 2291 (1980); Japanese Patent Laid-Open Publication No. 130660/1978; "J. Chem. Soc.", Perkin Trans. I. 1017 (1978); and East German Patent No. 127812).

Process (ii)

Compounds of formula (Ia) may also be prepared by reacting a compound having the general formula (IV):

(wherein $R^1$ and $R^2$ are as defined in general formula (I) and $Z^2$ is a halogen atom) with a compound having the general formula (V):

$$HS(CH_2)_m—B^1 \quad (V)$$

(wherein m and $B^1$ are as defined in general formulae (I) and (III), respectively) in the presence of hydrogenated metal, preferably hydrogenated sodium or sodium hydroxide, and in an inert solvent, e.g. N,N-dimethylformamide. It is noted that the synthesis of Compound (IV) may be carried out by known procedures (French Patent No. 2,152,345).

The compounds of general formula (I) wherein n=0 having the general formula (Ib):

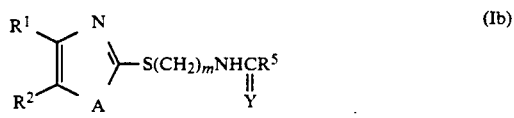

(wherein A, $R^1$, $R^2$, Y, $R^5$ and m are as defined in general formula (I)) may be obtained by any one of the following processes (iii), (iv) and (v).

Compound (Ib) is a general term of all compounds (Ib'), (Ib'') and (Ib''') obtained by processes (iii), (iv) and (v).

Process (iii)

A compound having the general formula (Ib'):

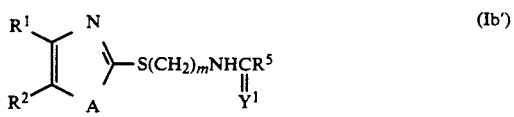

(wherein A, $R^1$, $R^2$ and m are as defined in general formula (I), $Y^1$ is an oxygen or sulfur atom, and $R^5$ represents a group —$NHR^6$ wherein $R^6$ is as defined in general formula (I)) may be prepared by reaction of a compound having the general formula (V):

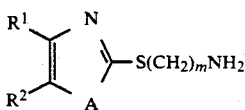

(wherein A, $R^1$, $R^2$ and m are as defined in general formula (I)) with a compound having the general formula (VI):

$$Y^1=C=R^{5a} \quad (VI)$$

(wherein $Y^1$ is a sulfur or oxygen atom and $R^{5a}$ represents a group $=NR^6$ in which $R^6$ is as defined in general formula in an alcohol such as ethanol.

Process (iv)

A compound having the following general formula (Ib''):

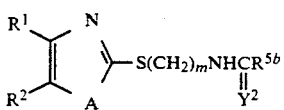

(wherein A, $R^1$, $R^2$ and m are as defined above, $Y^2$ is a group $=NCN$ or $=CHNO_2$, and $R^{5b}$ is a group $-SR^6$ where $R^6$ is as defined in general formula (I)) may be prepared by reaction of a compound having the above general formula (V) with a compound having the general formula (VII):

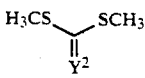

(wherein $Y^2$ is a group $=NCN$ or $=CHNO_2$) in an alcohol such as ethanol.

Process (v)

A compound having the general formula (Ib'''):

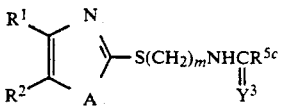

(wherein A, $R^1$, $R^2$ and m are as defined in general formula (I), $Y^3$ is a group $=NCN$ or $=CHNO_2$, and $R^5$ is a group $-NHR^6$ where $R^6$ is as defined in general formula (I)) may be prepared by reaction of compounds of formula (Ib'') obtained by process (iv) with a compound having the general formula (VIII):

$$H_2N-R^{5c} \quad (VIII)$$

(wherein $R^{5c}$ is a group $-NHR^6$ where $R^6$ is as defined in general formula (I)) in an inert solvent, e.g. methyl cellosolve.

Through the processes (i) to (v) it is possible to obtain the compounds of formula (I) wherein n=0, i.e. compounds of formulae (Ia) and (Ib).

The compounds of formula (I) wherein n=1 and 2 may be obtained from the compounds of formulae (Ia) and (Ib), prepared by the above processes.

A sulfoxide compound having the general formula (Ic):

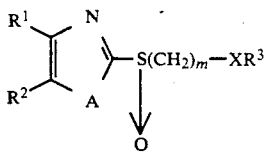

(wherein A, B, $R^1$, $R^2$ and m are as defined in general formula (I)) may be obtained by reacting the compound of general formulae (Ia) and (Ib) with 1 to 1.2 molar equivalents of an oxidizing agent in an inert solvent.

If the amount of the oxidizing agent is increased to 1 to 1.5 molar equivalents in the oxidizing reaction, then it is possible to obtain a sulfone compound having the general formula (Id):

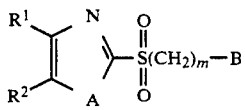

(wherein A, B, $R^1$, $R^2$ and m are as defined in general formula (I)).

The oxidizing agents used for these oxidizing reactions, for instance, may include peroxide derivatives such as hydrogen peroxide, m-chloroperbenzoic acid and sodium periodate, manganese dioxide, tertbutylhydroperoxide and N-bromosuccinimide. The solvents used, for example, may include water, acetic acid, a halogenated alkane such as methylene chloride, ketones such as acetone and other general-purpose solvents. Preferably, the oxidizing reactions may be carried out with hydrogen peroxide in acetic acid in the presence of sodium tungstate or with m-chloroperbenzoic acid in methylene chloride.

Use of Compounds/Antiulcerative Composition

The compounds according to the invention possess an antiulcerative activity and may be used as antiulcerative agents.

The antiulcerative composition containing the compounds of formula (I) or their salts as main ingredients may be generally available in the form of oral administration such as capsules, tablets and powders. These preparations may be formulated in conventional manners with ordinarily used vehicles, extenders, binders, wetting agents, disintegrators, surface active agents, lubricants, dispersants, buffers, preservatives, dissolution aids, and so on.

Although the dose varies dependent upon the conditions, age and sex of patients and other factors, the suitable daily dose as employed for an adult is 0.5 to 10 mg which may be conveniently administered in one or three doses.

The present invention will now be explained more specifically, but not exclusively, with reference to the following examples.

EXAMPLE 1

2-[(2-ethoxyethyl)thio]-4-(3-pyridyl)thiazole

Dissolved in 2.5 ml of N,N-dimethylformamide were 0.50 g of 2-mercapto-4-(3-pyridyl)-thiazole oxalate (1.82 mmol), and 0.10 g (4.17 mmol) of sodium hydride were added to the solution, which was stirred at room temperature. One hour later, 0.40 ml (3.65 mmol) of 2-chloroethyl ethyl ether were added to the suspension, which was then stirred for 2 hours at 80° C. The reaction solution was diluted with 50 ml of chloroform, followed by addition of 50 ml of a 5% saline solution and washing. After separation of the chloroform layer, the organic layer was dried over anhydrous magnesium sulfate, and concentrated in vacuo. The residues were then purified by silica gel chromatography to obtain 45 g of the title compound as an yellow oily form (93% yield).

$^1$H—NMRδ (CDCl$_3$): 1.22 (3H, t), 3.4–3.9 (6H, m), 7.33 (1H, ddd), 7.43 (1H, s), 8.16 (1H, ddd), 8.56 (1H, dd), 9.10 (1H, dd).
EI-MS m/s: 266 (M+), 194.

EXAMPLE 2

2-[(2-ethoxyethyl)sulfinyl]-4-(3-pyridyl)thiazole

Dissolved in 1.7 ml of acetic acid were 0.33 g (1.24 mmol) of the compound obtained in Example 1, and 0.15 ml (1.32 mmol) of a 30% aqueous solution of hydrogen peroxide and a catalytic amount of sodium tungstate were successively added to the solution, which was stirred at room temperature for 4 hours. The reaction solution was poured in 34 ml of water, neutralized with sodium hydrogencarbonate and extracted with 34 ml of chloroform. After separation of the chloroform layer, the organic layer was dried over anhydrous magnesium sulfate and concentrated in vacuo. The residues were purified by silica gel chromatography to obtain 0.27 g of white crystalline powders (77% yield).

$^1$H—NMRδ (CDCl$_3$): 1.16 (3H, t), 3.3–3.6 (4H, m), 3.94 (2H, t), 7.37 (1H, ddd), 7.86 (1H, s), 8.18 (1H, dt), 8.61 (1H, dd), 9.12 (1H, d).
EI-MS m/s: 282 (M+), 210, 194.

Examples 3–20 were performed according to either one of the procedures described in Examples 1 and 2, thereby obtained the following title compounds.

EXAMPLE 3

2-[(2-ethoxyethyl)thio]-4-(4-pyridyl)thiazole $^1$H—NMRδ CDCl$_3$): 1.22 (3H, t), 3.4–3.9 (6H, m), 7.57 (1H, s), 7.74 (2H, dd), 8.65 (2H, dd).
EI-MS m/s: 266 (M+), 194.

EXAMPLE 4

(2-ethoxyethyl)sulfinyl]-4-(4-pyridyl)thiazole $^1$H—NMRδ CDCl$_3$): 1.16 (3H, t), 3.3–3.6 (4H, m), 3.94 (2H, t), 7.79 (2H, d), 8.69 (2H, d).
EI-MS m/s: 282 (M+), 210, 194.

EXAMPLE 5

2-(2-[(2-ethoxyethyl)thio]-4-(2-pyridyl)thiazole $^1$H-NMRδ CDCl$_3$): 1.22 (3H, t), 3.4–3.9 (6H, m), 7.1–7.3 (1H, m), 7.7–8.0 (1H, m), 7.96 (1H, s), 8.10 (1H, d), 8.5–8.6 (1H, m).
EI-MS m/s: 266 (M+), 194.

EXAMPLE 6

2-[(2-ethoxyethyl)sulfinyl]-4-(2-pyridyl)thiazole $^1$H-NMRδ CDCl$_3$): 1.17 (3H, t), 3.3–3.7 (4H, m), 3.9–4.0 (2H, m), 7.2–7.3 (1H, m), 7.7–7.9 (1H, m), 8.08 (1H, s), 8.6–8.7 (1H, m).
EI-MS m/s: 282 (M+), 210, 194.

EXAMPLE 7

2-[(2-diisopropylaminoethyl)thio]-4-(3-pyridyl)thiazole $^1$H-NMRδ CDCl$_3$): 1.05 (12H, d), 2.8–3.4 (6H, m}, 7.32 (1H, ddd), 7.41 (1H, s), 8.16 (1H, dt), 8.55 (1H, dd), 9.10 (1H, dd).
EI-MS m/s: 322 (M+ +1), 221, 194.

EXAMPLE 8

2-[(2-diisopropylaminoethyl)sulfinyl-1- 4 - (3 -pyridyl)thiazole $^1$H-NMRδ CDCl$_3$): 1.05 (12H, dd), 3.0–3.3 (6H, m), 7.36 (1H, ddd), 7.85 (1H, s), 8.17 (1H, dt), 8.61 (1H, dd), 9.13 (1H, dd).
EI-MS m/s: 338 (M+ +1), 210, 194.

EXAMPLE 9

2-[(2-ethoxyethyl)thio]-4-phenylthiazole $^1$H-NMRδ CDCl$_3$): 1.21 (3H, t), 3.4–3.9 (6H, m), 7.3–7.4 (3H, m), 7.33 (1H, s), 7.8–7.9 (2H, m}.
EI-MS m/s: 265 (M+), 193.

EXAMPLE 10

2-[(2-ethoxyethyl)sulfinyl]-4-phenylthiazole $^1$H-NMRδ CDCl$_3$): 1.17 (3H, t), 3.3–3.7 (4H, m), 3.9–4.0 (2H, m), 7.3–7.5 (3H, m), 7.74 (1H, s), 7.8–7.9 (2H, m).
EI-MS m/s: 281 (M+), 209, 193.

EXAMPLE 11

2-[(2-ethoxyethyl))thio]-5-phenylthiazole $^1$H-NMRδ (CDCl3): 1.21 (3H, t), 3.4–3.8 (6H, m), 7.3–7.5 (5, m), 7.79 (1H, s).
EI-MS m/s: 265 (M+), 193.

EXAMPLE 12

2-[(2-ethoxyethyl)sulfinyl]-5-phenylthiazole $^1$H-NMRδ CDCl$_3$): 1.16 (3H, t), 3.3–3.6 (4H, m), 3.9–4.0 (2H, m), 7.4–7.6 (5H, m), 8.04 (1H, s).
EI-MS m/s: 281 (M+), 209, 193.

EXAMPLE 13

2-[(2-ethoxyethyl)thio]-4-(3-thienyl)thiazole $^1$H-NMRδ CDCl$_3$): 1.21 (3H, t), 3.4–3.9 (6H, m), 7.17 (1H, s), 7.3–7.5 (2H, m), 7.7–7.8 (1H, m).
EI-MS m/s: 271 (M+), 199.

EXAMPLE 14

2-[(2-ethoxyethyl)sulfinyl]-4-(3-thienyl)thiazole $^1$H-NMRδ CDCl$_3$): 1.17 (3H, t), 3.3–3.6 (4H, m), 3.9–4.0 (2H, m), 7.4–7.5 (2H, m), 7.58 (1H, s), 7.7–7.8 (1H, m).
EI-MS m/s: 287 (M+), 215, 199.

EXAMPLE 15

2-[(2-ethoxyethyl)thio]-4-(2-thienyl)thiazole $^1$H-NMRδ (CDCl$_3$): 1.21 (3H, t), 3.4–3.9 (6H, m), 7.04 (1H, dd), 7.18 (1H, s), 7.26 (1H, dd), 7.42 (1H, dd).
EI-MS m/s: 271 (M+), 199.

EXAMPLE 16

2-[2-ethoxyethyl)sulfinyl]-4-(2-thienyl)thiazole $^1$H-NMR$\delta$ CDCl$_3$): 1.17 (3H, t), 3.3–3.6 (4H, m), 3.9–4.0 (2H, m), 7.07 (1H, dd), 7.32 (1H, dd), 7.46 (1H, dd), 7.59 (1H, s).
EI-MS m/s: 287 (M+), 215, 199.

EXAMPLE 17

2-(2-ethoxyethyl)thio]-4-(2-furanyl)thiazole $^1$H-NMR$\delta$ CDCl$_3$): 1.21 (3H, t), 3.4–3.9 (6H, m), 6.46 (1H, dd), 6.77 (1H, d), 7.27 (1H, s), 7.42 (1H, dd).
EI-MS m/s: 255 (M+), 183.

EXAMPLE 18

2-[(2-ethoxyethyl)sulfinyl]-4-(2-furanyl)thiazole $^1$H-NMR$\delta$ CDCl$_3$): 1.16 (3H, t), 3.3–3.6 (4H, m), 3.9–4.0 (2H, m), 6.49 (1H, dd), 6.81 (1H, d), 7.46 (1H, dd), 7.66 (1H, s).
EI-MS m/s: 271 (M+), 199, 183.

EXAMPLE 19

2-[(2-ethoxyethyl)thio]-4-(2-thiazolyl)thiazole $^1$H-NMR$\delta$ CDCl$_3$): 1.22 (3H, t), 3.4–3.9 (6H, m), 7.34 (1H, d), 7.83 (1H, d), 7.84 (1H, s).
EI-MS m/s: 272 (M+), 200.

EXAMPLE 20

2-[(2-ethoxyethyl)sulfinyl]-4-(2-thiazolyl)thiazole $^1$H-NMR$\delta$ CDCl$_3$): 1.16 (3H, t), 3.4–3.6 (4H, m), 3.93 (2H, t), 7.40 (1H, d), 7.87 (1H, d), 8.22 (1H, s).
EI-MS m/s: 288 (M+), 216, 200.

EXAMPLE 21

N-(5-chlorobenzothiazol-2-yl)thioethyl—N'-ethylurea

Dissolved in 10 ml of ethanol was 1.00 g (4.09 mmol) of 2-(2-aminoethylthio)-5-chlorobenzothiazole, and 0.36 ml (4.55 mmol) of ethyl isocyanate were added to the solution, which was stirred at room temperature for 15 minutes. The precipitated white crystals were then filtered out to obtain 1.15 g of the title compound (89% yield).

$^1$H-NMR$\delta$ CDCl$_3$): 0.97 (3H, t), 2.9–3.2 (2H, m), 3.3–3.4 (4H, m), 5.8–5.9 (1H, br), 6.1–6.2 (1H, br), 7.41 (1H, dd), 7.91 (1H, d), 8.04 (1H, d).
EI-MS m/s: 315 (M+), 229, 201.

EXAMPLE 22

N-(5-chlorobenzothiazol-2-yl)sulfinylethyl—N'-ethylurea

Dissolved in a mixed solution of 5.8 ml of acetic acid and 5.8 ml of methylene chloride were 1.15 g (3.65 mmol) of the compound obtained in Example 21, and 0.41 ml (4.02 mmol) of a 30% aqueous solution of hydrogen peroxide and a catalytic quantity of sodium tungstate were successively added to the solution, which was stirred at room temperature for 1 hour. The reaction solution was poured in 116 ml of water, neutralized with sodium hydrogencarbonate and extracted with 116 ml of chloroform. After separation of the chloroform layer, the organic layer was dried over anhydrous magnesium sulfate and concentrated in vacuo. The residues were purified by silica gel chromatography to obtain 0.96 g of white crystalline powders (79% yield).

$^1$H-NMR$\delta$ (CDCl$_3$): 0.93 (3H, t), 2.8–3.1 (2H, m), 3.4–3.5 (4H, m), 5.9–6.0 (1H, br), 6.2–6.3 (1H, br), 7.61 (1H, dd), 8.20 (1H, d), 8.31 (1H, d).
EI-MS m/s: 331 (M+), 201.

Examples 23–25 were performed according to either one of the procedures described in Examples 21 or 22 to obtain the title compounds.

EXAMPLE 23

N-(5-chlorobenzothiazol-2-yl)thioethyl—N'-(2-chloroethyl)urea $^1$H-NMR$\delta$ (CDCl$_3$): 3.3–3.5 (8H, m), 6.2–6.4 (2H, br), 7.36 (1H, dd), 7.87 (1H, d), 7,99 (1H, d).
EI-MS m/s: 349 (M+), 228, 201.

EXAMPLE 24

N-(5-chlorobenzothiazol-2-yl)sulfinylethyl—N'-(2-chloroethyl)urea $^1$H NMR$\delta$ (CDCl$_3$): 3.2–3.5 (8H, m), 6.2–6.4 (2H, br), 7.61 (1H, dd), 8.19 (1H, d), 8.31 (1H, d).
EI-MS m/s: 365 (M+), 201.

EXAMPLE 25

N-(5-chlorobenzothiazol-2-yl)thioethyl—N'-ethylthiourea $^1$H-NMR$\delta$ CDCl$_3$): 1.19 (3H, t), 3.4–3.6 (4H, m), 3.9–4.1 (2H, m), 6.4–6.5 (1H, br), 6.8–6.9 (1H, br), 7.29 (1H, dd), 7.67 (1H, d), 7.78 (1H, d).
EI-MS m/s: 331 (M+), 228, 201.

EXAMPLE 26

N-(5-chlorobenzothiazol-2-yl)thioethyl—N'-cyano-S-methylisourea

Dissolved in 20 ml of ethanol was 1.19 g (8.18 mmol) of 2-(2-aminoethylthio)-5-chlorobenzothiazole, and 25 ml of an ethanol solution of 2.00 g (8.18 mmol) of N-cyano-S,S'-dimethyldithioiminocarbonate were added to the solution, which was stirred overnight at room temperature. The precipitated white crystals were filtered out to obtain 2.67 g of the title compound (95% yield).

$^1$H-NMR$\delta$ CDCl$_3$): 2.50 (3H, s), 3.6–3.7 (4H, m), 7.42 (1H, dd), 7.91 (1H, d), 8.05 (1H, d), 8.0–8.1 (1H, br).
EI-MS m/s: 342 (M+), 228, 201.

EXAMPLE 27

N-(5-chlorobenzothiazol-2-yl)thioethyl—N'-cyano—N''-ethylguanidine

Dissolved in 80 ml of methyl cellosolve were 1.60 g (4.67 mmol) of the compound obtained in Example 26, and 42 ml of a methyl cellosolve solution of 4.20 g (93.3 mmol) of ethylamine were added to the solution, which was heated with stirring at 80° C. for 4 hours. The solvent was removed in vacuo and the residue was purified by silica gel chromatography to obtain 0.56 g of white crystalline powders (35% yield).

$^1$H-NMR$\delta$ (CDCl$_3$): 0.97 (3H, t), 3.0–3.1 (2H, m), 3.4–3.5 (4H, m), 6.9–7.0 (1H, br), 7.1–7.2 (1H, br), 7.37 (1H, dd), 7.99 (1H, d).
EI-MS m/s: 339 (M+), 228, 201.

EXAMPLE 28

N-(5-chlorobenzothiazol-2-yl)sulfinylethyl—N'-cyano—N''-ethylguanidine

Dissolved in 8 ml of methylene chloride were 0.20 g (0.59 mmol) of the compound obtained in Example 27, and 0.15 g (0.59 mmol) of m-chloroperbenzoic acid with a 70% purity were added to the solution, which was stirred at room temperature for 2 hours. The solvent was removed in vacuo and the residue was purified by silica gel chromatography to obtain 0.20 g of white crystalline powders (95% yield).

$^1$H-NMR$\delta$ CDCl$_3$): 1.21 (3H, t), 3.1–3.9 (6H, m), 5.8–5.9 (1H, br), 6.4–6.5 (1H, br), 7.48 (1H, dd), 7.92 (1H, d), 8.06 (1H, d).

EI-MS m/s: 355 (M+), 201.

Examples 29–30 were performed according to either one of the procedures described in Examples 26 and 27 to obtain the title compounds.

EXAMPLE 29

1-(5-chlorobenzothiazol-2-yl)thioethylamino-1-methylthio-2-nitroethene $^1$H-NMR$\delta$ CDCl$_3$): 2.45 (3H, s), 3.6–3.8 (4H, m), 6.5–6.6 (1H, br), 7.39 (1H, dd), 7.94 (1H, br), 8.01 (1H, d).

EI-MS m/s: 361 (M+), 228, 201.

EXAMPLE 30

N-(5-chlorobenzothiazol-2-yl)thioethyl—N'-ethyl-2-nitro-1,1-ethenediamine $^1$H-NMR$\delta$ (CDCl$_3$): 1.12 (3H, t), 3.1–3.4 (2H, m), 3.5–3.6 (4H, br), 7.43 (1H, ddd), 8.05 (1H, d), 8.15 (1H, br).

EI-MS m/s: 358 (M+), 228, 201.

EXAMPLE 31

5-chloro-2-[(2-morpholinoethyl)thio]benzothiazole

Dissolved in 5 ml of N,N-dimethylformamide was 1.00 g (5.0 mmol) of 5-chloro-2-mercaptobenzothiazole, and 0.26 g (10.8 mmol) of hydrogenated sodium were added to the solution, which was stirred at room temperature. One hour later, 0.93 g (5.0 mmol) of a hydrochloride of 2-chloroethylmorpholine were added to the suspension, which was then stirred for 2 hours at 80° C. The solution was diluted with 100 ml of chloroform, followed by addition of 100 ml of a 5% saline solution and washing. After separation of the chloroform layer, the organic layer was dried over anhydrous magnesium sulfate and concentrated in vacuo. The residues were purified by silica gel chromatography to obtain 1.05 g of white crystalline powders (67% yield).

$^1$H-NMR$\delta$ CDCl$_3$): 2.5–2.6 (4H, m), 2.78 (2H, t), 3.52 (2H, t), 3.7–3.8 (4H, m), 7.25 (1H, dd), 7.64 (1H, d), 7.82 (1H, d).

EI-MS m/s: 314 (M+), 228, 201.

EXAMPLE 32

5-chloro-2-[(2-morpholinoethyl)sulfinyl]benzothiazole

Dissolved in 4 ml of acetic acid were 0.80 g (2.5 mmol) of the compound obtained in Example 31, and 0.37 ml (3.3 mmol) of a 30% aqueous solution of hydrogen peroxide and a catalytic quantity of sodium tungstate were successively added to the solution, which was stirred at room temperature for 1 hour. The solution was poured in 80 ml of water, neutralized with sodium hydrogencarbonate and extracted with 80 ml of chloroform. After separation of the chloroform layer, the organic layer was dried over anhydrous magnesium sulfate, and concentrated in vacuo. The residues were purified by silica gel chromatography to obtain 0.52 g of the title compound in the form of white crystalline powders (62% yield).

$^1$H-NMR$\delta$ CDCl$_3$): 2.46 (4H, t), 2.90 (2H, t), 3.3–3.5 (6H, m), 7.45 (1H, dd), 7.92 (1H, d), 8.01 (1H, d).

EI-MS m/s: 330 (M+), 217, 201.

Dissolved in 10 ml of chloroform were 0.50 g (1.51 ml) of the title compound, and 0.25 ml of 6N hydrochloric acid/dioxane were added to the solution to precipitate white crystals, which were filtered out to obtain 0.46 g of a hydrochloride of the title compound.

$^1$H-NMR$\delta$ (D$_2$O): 3.3–3.4 (4H, m), 3.5–3.7 (2H, m), 3.8–4.0 (6H, m), 7.62 ((1H, dd), 8.07 (1H, s), 8.14 (1H, d).

EI-MS m/s: 330 (M+), 217.

EXAMPLE 33

5-chloro-2-[(2-morpholinoethyl)sulfonyl]benzothiazole

Dissolved in 1 ml of acetic acid were 0.20 g (0.64 mmol) of the compound obtained in Example 31, and 0.18 ml (1.50 mmol) of a 30% aqueous solution of hydrogen peroxide and a catalytic quantity of sodium tungstate were successively added to the solution for one-hour reaction. By subsequently following the procedure of Example 32, 0.18 g of the title compound in the form of white crystalline powders were obtained (82% yield).

$^1$H-NMR$\delta$ CDCl$_3$): 2.3–2.4 (4H, m), 2.90 (2H, t), 3.1–3.2 (4H, m), 3.72 (2H, t), 7.52 (1H, dd), 7.95 (1H, d), 8.16 (1H, d).

EI-MS m/s: 347 (M++1), 260, 169.

Examples 34–78 were performed according to any one of the procedures described in Examples 31–33, thereby obtaining the title compounds.

EXAMPLE 34

7-chloro-2-[(2-morpholinoethyl)thio]benzothiazole $^1$H-NMR$\delta$ CDCl$_3$): 2.5–2.6 (4H, m), 2.7–2.9 (2H, m), 3.4–3.6 (2H, m), 3.6–3.8 (4H, m), 7.29 (1H, d), 7.44 (1H, t), 7.73 (1H, dd).

EI-MS m/s: 314 (M+), 228, 201.

EXAMPLE 35

7-chloro-2-[(2-morpholinoethyl)sulfinyl]benzothiazole $^1$H-NMR$\delta$ CDCl$_3$): 2.45 (4H, t), 2.8–3.0 (2H, m), 3.3–3.5 (6H, m), 7.48 (1H, d), 7.52 (1H, t), 7.93 (1H, dd).

EI-MS m/s: 330 (M+), 217, 201.

EXAMPLE 36

6-chloro-2-[(2-morpholinoethyl)thio]benzothiazole $^1$H-NMR$\delta$ CDCl$_3$): 2.5–2.6 (4H, m), 2.78 (2H, t), 3.52 (2H, t), 3.7–3.8 (4H, m), 7.35 (1H, dd), 7.71 (1H, d), 7.74 (1H, d).

EI-MS m/s: 314 (M+), 228, 201.

EXAMPLE 37

6-chloro-2-[(2-morpholinoethyl)sulfinyl]benzothiazole $^1$H-NMR$\delta$ CDCl$_3$): 2.46 (4H, t), 2.90 (2H, t), 3.3–3.5 (6H, m), 7.51 (1H, dd), 7.94 (1H, d), 7.98 (1H, d).

EI-MS m/s: 330 (M+), 217, 201.

EXAMPLE 38

4-chloro-2-[(2-morpholinoethyl)thio]benzothiazole $^1$H-NMRδ CDCl$_3$): 2.5–2.6 (4H, m), 2.82 (2H, t), 3.5–3.8 (6H, m), 7.18 (1H, t), 7.42 (1H, dd), 7.63 (1H, dd).

EI-MS m/s: 314 (M+), 228, 201.

EXAMPLE 39

4-chloro-2-[(2-morpholinoethyl)sulfinyl]benzothiazole $^1$H-NMRδ CDCl$_3$): 2.45 (4H, t), 2.8–3.0 (2H, m), 3.4–3.5 (6H, m}, 7.39 (1H, t), 7.58 (1H, dd), 7.90 (1H, dd).

EI-MS m/s: 330 (M+), 217, 201.

EXAMPLE 40

5-chloro-2-[(2-piperidinoethyl)thio]benzothiazole $^1$H-NMRδ CDCl$_3$): 1.5–1.6 (6H, br), 2.4–2.5 (4H, br), 2.7–2.8 (2H, m), 3.4–3.6 (2H, m), 7.24 (1H, dd), 7.63 (1H, d), 7.82 (1H, d).

EI-MS m/s: 312 (M+), 228, 201.

EXAMPLE 41

5-chloro-2-[(2-piperidinoethyl)sulfinyl]-benzothiazole $^1$H-NMRδ CDCl$_3$): 1.4–1.5 (6H, br), 2.3–2.4 (4H, br), 2.8–2.9 (2H, m), 3.3–3.4 (2H, m), 7.44 (1H, dd), 7.91 (1H, d), 8.03 (1H, d).

EI-MS m/s: 328 (M+), 216, 201.

EXAMPLE 42

5-chloro-2-{[2-(1-pyrodinyl)ethyl]thio}benzothiazole $^1$H-NMRδ CDCl$_3$): 1.8–1.9 (4H, m), 2.5–2.6 (4H, m), 2.8–3.0 (2H, m), 3.4–3.6 (2H, m), 7.24 (1H, dd), 7.63 (1H, d), 7.83 (1H, d).

EI-MS m/s: 298 (M+), 228, 201.

EXAMPLE 43

5-chloro-2-{[2-(1-pyrodinyl)ethyl]sulfonyl}benzothiazole $^1$H-NMRδ CDCl$_3$):

1.6–1.7 (4H, m), 2.5–2.6 (4H, m), 2.9–3.4 (4H, m), 7.44 (1H, dd), 7.90 (1H, d), 8.02 (1H, d).

EI-MS m/s: 314 (M+), 228, 201.

EXAMPLE 44

5-chloro-2-[[2-tetrahydropyranyl)methylthio]benzothiazole $^1$H-NMRδ CDCl$_3$): 1.4–1.9 (6H, br), 3.3–3.7 (4H, m), 3.9–4.1 (1H, br), 7.22 (1H, dd), 7.60 (1H, d), 7.80 (1H, d).

EI-MS m/s: 299 (M+), 215, 201.

EXAMPLE 45

5-chloro-2-[(2-tetrahydropyranyl)methylsulfinyl]benzothiazole $^1$H-NMRδ CDCl$_3$): 1.5–1.7 (6H, br), 3.2–4.1 (5H, m), 7.44 (1H, dd), 7.90 (1H, d), 8.04 (1H, d).

EI-MS m/s: 315 (M+), 217, 201.

EXAMPLE 46

5-chloro-2-{[2-(N-methylpyrrolidin-2-yl)ethyl]thio}benzothiazole $^1$H-NMRδ CDCl$_3$): 1.6–2.4 (8H, m), 2.33 (3H, s), 3.0–3.5 (3H, m), 7.25 (1H, dd), 7.64 (1H, d), 7.83 (1H, d).

EI-MS m/s: 312 (M+), 228, 200.

EXAMPLE 47

5-chloro-2-{[2-(N-methylpyrrolidin-2-Y1)ethyl]sulfinyl}benzothiazole $^1$H-NMRδ CDCl$_3$): 1.5–2.3 (8H, m), 2.27 (3H, d), 3.0–3.3 (3H, m), 7.46 (1H, dd), 7.95 (1H, d), 8.05.(1H, d).

EI-MS m/s: 328 (M+), 216, 201.

EXAMPLE 48

5-chloro-2-[(2-morpholinoethyl)thio]benzimidazole $^1$H-NMRδ CDCl$_3$): 2.6–2.7 (4H, m), 2.9–3.0 (2H, m), 3.2–3.3 (2H, m), 3.8–3.9 (4H, m), 7.14 (1H, dd), 7.3–7.6 (2H, br).

EI-MS m/s: 297 (M+), 211, 184.

EXAMPLE 49

5-chloro-2-[(2-morpholinoethyl)sulfinyl]benzimidazole $^1$H-NMRδ CDCl$_3$): 2.46 (4H, t), 2.92 (2H, t), 3.4–3.6 (6H, m), 7.29 (1H, dd), 7.59 (1H, d), 7.65 (1H, d).

EI-MS m/s: 313 (M+), 200, 184.

EXAMPLE 50

2[(2-morpholinoethyl)thio]benzimidazole $^1$H-NMRδ CDCl$_3$): 2.6–2.7 (4H, m), 2.8–3.0 (2H, m), 3.2–3.3 (2H, m), 3.8–3.9 (4H, m), 7.17 (2H, dd), 7.3–7.7 (2H, br).

EI-MS m/s: 263 (M+), 177, 150.

EXAMPLE 51

2-[(2-morpholinoethyl)sulfinyl]benzimidazole $^1$H-NMRδ CDCl$_3$) 2.45 (4H, t), 2.91 (2H, t), 3.4–3.6 (6H, m), 7.32 (2H, dd), 7.6–7.7 (2H, br).

EI-MS m/s: 279 (M+), 166, 150.

EXAMPLE 52

5-methoxy-2-[(2-morpholinoethyl)thio]benzimidazole $^1$H-NMRδ CDCl$_3$): 2.6–2.7 (4H, m), 2.8–3.0 (2H, m), 3.2–3.3 (2H, m), 3.8–3.9 (4H, m), 3.83 (3H, s), 6.83 (1H, dd), 7.0 (1H, br), 7.41 (1H, d, br).

EI-MS m/s: 293 (M+), 180.

EXAMPLE 53

5-methoxy-2-[(2-morpholinoethyl)sulfinyl]benzimidazole $^1$H-NMRδ CDCl$_3$): 2.2–2.5 (4H, m), 2.89 (2H, t), 3.4–3.6 (6H, m), 3.86 (3H, s), 6.97 (1H, dd), 7.1 (1H, br), 7.56 (1H, d, br).

EI-MS m/s: 309 (M+), 196, 180.

EXAMPLE 54

5-fluoro-2-[(2-morpholinoethyl)thio]benzothiazole $^1$H-NMRδ CDCl$_3$): 2.5–2.6 (4H, m), 2.79 (2H, t), 3.53 (2H, t), 3.7–3.8 (4H, m), 7.05 (1H, dt), 7.53 (1H, dd), 7.65 (1H, dd).

EI-MS m/s: 298 (M+), 212, 185.

EXAMPLE 55

5-fluoro-2-[(2-morpholinoethyl)sulfinyl]benzothiazole $^1$H-NMRδ CDCl$_3$): 2.46 (4H, t), 2.91 (2H, t), 3.3–3.5 (6H, m), 7.26 (1H, dt), 7.71 (1H, dd), 7.94 (1H, dd).

EI-MS m/s: 314 (M+}, 201, 185.

EXAMPLE 56

5-trifluoromethyl-2-[(2-morpholinoethyl)thio]benzothiazole

¹H-NMRδ CDCl₃): 2.5–2.6 (4H, m), 2.7–2.9(2H, m), 3.5–3.6 (2H, m), 3.7–3.8 (4H, m), 7.51 (1H, dd), 7.84 (1H, dd), 8.08 (1H, s).
EI-MS m/s: 348 (M+), 262, 235.

EXAMPLE 57

5-trifluoromethyl-2-[(2-morpholinoethyl)sulfinyl]benzothiazole

¹H-NMRδ CDCl₃): 2.47 (4H, t), 2.92 (2H, t), 3.3–3.5 (6H, m), 7.72 (1H, dd), 8.14 (1H, d), 8.30 (1H, s). 25
EI-MS m/s: 364 (M+), 251, 235.

EXAMPLE 58

5-nitro-2-[(2-morpholinoethyl)thio]benzothiazole

¹H-NMRδ CDCl₃): 2.55 (4H, t), 2.82 (2H, t), 3.59 (2H, t), 3.72 (4H, t), 7.84 (1H, d), 8.17 (1H, dd), 8.65 (1H, d).
EI-MS m/s: 326 (M++1), 239, 212.

EXAMPLE 59

5-nitro-2-[(2-morpholinoethyl)sulfinyl]benzothiazole

¹H-NMRδ CDCl₃): 2.47 (4H, t), 2.9–3.0 (2H, m), 3.4–3.5 (6H, m), 8.15 (1H, d), 8.27 (1H, dd), 8.88 (1H, d).
EI-MS m/s: 341 (M+), 228, 212.

EXAMPLE 60

7-chloro-2-[(2-ethoxyethyl)thio]benzothiazole

¹H-NMRδ CDCl₃): 1.22 (3H, t), 3.5–3.9 (6H, m), 7.29 (1H, d), 7.35 (1H, t), 7.73 (1H, dd).
EI-MS m/s: 273 (M+), 201.

EXAMPLE 61

7-chloro-2-[(2-ethoxyethyl)sulfinyl]benzothiazole

¹H-NMRδ CDCl₃): 1.07 (3H, t), 3.3–3.6 (4H, m), 3.94 (2H, t), 7.49 (1H, d), 7.50 (1H, t), 7.96 (1H, d).
EI-MS m/s: 289 (M+), 217, 169.

EXAMPLE 62

6-chloro-2-[(2-ethoxyethyl)thio]benzothiazole

¹H-NMRδ CDCl₃): 1.22 (3H, t), 3.4–3.9 (6H, m), 7.35 (1H, dd), 7.71 (1H, d), 7.74 (1H, d).
EI-MS m/s: 273 (M+), 201.

EXAMPLE 63

6-chloro-2-[(2-ethoxyethyl)sulfinyl]benzothiazole

¹H-NMRδ CDCl₃): 1.08 (3H, t), 3.3–3.6 (4H, m), 3.94 (2H, t), 7.51 (1H, dd), 7.97 (1H, d), 7.98 (1H, d).
EI-MS m/s: 289 (M+), 217, 169.

EXAMPLE 64

4-chloro-2-[(2-ethoxyethyl)thio]benzothiazole

¹H-NMRδ CDCl₃): 1.22 (3H, t), 3.5–3.9 (6H, m), 7.18 (1H, t), 7.42 (1H, dd), 7.62 (1H, dd).
EI-MS m/s: 273 (M+), 201.

EXAMPLE 65

4-chloro-2-[(2-ethoxyethyl)sulfinyl]benzothiazole

¹H-NMRδ (CDCl₃): 1.08 (3H, t), 3.4–3.6 (4H, m), 3.89 (2H, t), 7.39 (1H, t), 7.58 (1H, dd), 7.90 (1H, dd).
EI-MS m/s: 289 (M+), 217, 169.

EXAMPLE 66

5-chloro-2-{[2-(2-chloroethoxy)ethyl]thio}benzothiazole

¹H-NMRδ CDCl₃): 3.5–4.0 (8H, m), 7.26 (1H, dd), 7.64 (1H, d), 7.83 (1H, d).
EI-MS m/s: 307 (M+), 201.

EXAMPLE 67

5-chloro-2-{[2-(2-chloroethoxy)ethyl]sulfinyl}benzothiazole

¹H-NMRδ CDCl₃): 3.4–3.8 (6H, m), 4.03 (2H, t), 7.46 (1H, dd), 7.91 (1H, d), 8.05 (1H, d).
EI-MS m/s: 323 (M+), 217, 169.

EXAMPLE 68

5-chloro-2-{2-(2-chloroethoxy)ethyl]sulfonyl]benzothiazole

¹H-NMRδ CDCl₃):

3.3–3.4 (2H, m), 3.6–3.7 (2H, m), 3.7–3.9 (2H, m), 4.0–4.1 (2H, m), 7.50 (1H, dd), 7.94 (1H, d), 8.20 (1H, d).
EI-MS m/s: 339 (M+), 260, 169.

EXAMPLE 69

5-chloro-2-[(2-ethoxyethyl)thio]benzimidazole

¹H-NMRδ (CDCl₃): 1.32 (3H, t), 3.34 (2H, t), 3.66 (2H, q), 3.88 (2H, t), 7.14 (1H, dd), 7.3 (1H, br), 7.5 (1H, br), 11–11.5 (1H, br).
EI-MS m/s: 256 (M+), 183.

EXAMPLE 70

5-chloro-2-[(2-ethoxyethyl)sulfinyl]benzimidazole

¹H-NMRδ (CDCl₃): 1.09 (3H, t), 3.4–3.6 (4H, m), 3.9–4.0 (2H, m), 7.29 (1H, dd), 7.5–7.8 (2H, br), 12.3 (1H, br).
EI-MS m/s: 272 (M+), 200, 184.

EXAMPLE 71

5-methoxy-2-[(2-ethoxyethyl)thio]benzimidazole

¹H-NMRδ CDCl₃): 1.29 (3H, t), 3.33 (2H, t), 3.59 (2H, t), 3.7–3.9 (2H, m), 3.81 (3H, s), 6.82 (1H, dd), 7.0 (1H, br), 7.3–7.4 (1H, br), 11.2 (1H, br).
EI-MS m/s: 252 (M+), 180.

EXAMPLE 72

5-methoxy-2-[(2-ethoxyethyl)sulfinyl]benzimidazole

¹H-NMRδ CDCl₃): 1.11 (3H, t), 3.4–3.6 (4H, m), 3.86 (3H, s), 3.93 (2H, t), 6.9–7.7 (3H, m, br), 12.0 (1H, br).
EI-MS m/s: 268 (M+), 195, 180.

EXAMPLE 73

5-fluoro-2-[(2-ethoxyethyl)thio]benzothiazole

¹H-NMRδ CDCl₃) 1.22 (3H, t), 3.4–3.9 (6H, m), 7.04 (1H, dt), 7.53 (1H, dd), 7.65 (1H, dd).
EI-MS m/s: 257 (M+), 185.

EXAMPLE 74

5-fluoro-2-[(2-ethoxyethyl)sulfinyl]benzothiazole

¹H-NMRδ CDCl₃) 1.08 (3H, t), 3.3–3.6 (4H, m), 3.94 (2H, t), 7.25 (1H, dt), 7.73 (1H, dd), 7.93 (1H, dd).
EI-MS m/s: 273 (M+), 200, 153.

EXAMPLE 75

5-trifluoromethyl-2-[(2-ethoxyethyl)thio]benzothiazole $^1$H-NMRδ CDCl$_3$): 1.22 (3H, t), 3.5–3.9 (6H, m), 7.51 (1H, dd), 7.83 (1H, d), 8.10 (1H, d).
EI-MS m/s: 307 (M+), 235.

EXAMPLE 76

5-trifluoromethyl-2-[(2-ethoxyethyl)sulfinyl]benzothiazole $^1$H-NMRδ CDCl$_3$): 1.06 (3H, t), 3.4–3.6 (4H, m), 3.95 (2H, t), 7.71 (1H, dd), 8.13 (1H, d), 8.33 (1H, s).
EI-MS m/s: 323 (M+), 251, 203.

EXAMPLE 77

5-nitro-2-[(2-ethoxyethyl)thio]benzothiazole $^1$H-NMRδ CDCl$_3$): 1.23 (3H, t), 3.5–3.9 (6H, m), 7.90 (1H, d), 8.18 (1H, dd), 8.67 (1H, d).
EI-MS m/s: 284 (M+), 212.

EXAMPLE 78

5-nitro-2-[(2-ethoxyethyl)sulfinyl]benzothiazole $^1$H-NMRδ CDCl$_3$): 1.03 (3H, t), 3.4–3.6 (4H, m), 3.97 (2H, t), 8.16 (1H, d), 8.37 (1H, dd), 8.89 (1H, s).
EI-MS m/s: 300 (M+), 228.

The following example illustrates pharmaceutical compositions according to the present invention. The term "active ingredient" is used to represent a compound of formula (I).

EXAMPLE 79

| (Pharmaceutical Composition) | mg/tablet |
|---|---|
| (a) Oral tablet | |
| Active Ingredient | 15 |
| Lactose | 49.2 |
| Starch | 30 |
| Polyvinylpyrrolidone | 6 |
| Microcrystalline Cellulose | 18 |
| Colloidal Silica | 1.2 |
| Magnesium Stearate | 0.6 |
| Total | 120 |
| (b) Oral Capsule | |
| Active Ingredient | 25 |
| Lactose | 100 |
| Starch | 13 |
| TC-5 | 10 |
| Magnesium Stearate | 2 |
| Total | 150 |

The structures of the above-mentioned compounds are set out in Tables 1 and 2.

TABLE 1

| Example | R$^1$ | R$^2$ | A | B | m | n |
|---|---|---|---|---|---|---|
| 1 | 4-pyridyl | H | S | —OEt | 2 | 0 |
| 2 | 3-pyridyl | H | S | —OEt | 2 | 1 |
| 3 | 4-pyridyl | H | S | —OEt | 2 | 0 |
| 4 | 3-pyridyl | H | S | —OEt | 2 | 1 |
| 5 | 2-pyridyl | H | S | —OEt | 2 | 0 |
| 6 | 2-pyridyl | H | S | —OEt | 2 | 1 |
| 7 | 3-pyridyl | H | S | —N(i-Pr)$_2$ | 2 | 0 |
| 8 | 3-pyridyl | H | S | —N(i-Pr)$_2$ | 2 | 1 |
| 9 | ph | H | S | —OEt | 2 | 0 |
| 10 | ph | H | S | —OEt | 2 | 1 |
| 11 | H | ph | S | —OEt | 2 | 0 |
| 12 | H | ph | S | —OEt | 2 | 1 |
| 13 | 2-thienyl | H | S | —OEt | 2 | 0 |
| 14 | 2-thienyl | H | S | —OEt | 2 | 1 |
| 15 | 2-thienyl | H | S | —OEt | 2 | 0 |
| 16 | 2-thienyl | H | S | —OEt | 2 | 1 |
| 17 | 2-furyl | H | S | —OEt | 2 | 0 |
| 18 | 2-furyl | H | S | —OEt | 2 | 1 |
| 19 | isothiazolyl | H | S | —OEt | 2 | 0 |

TABLE 1-continued

| Example | R¹ | R² | A | B | m | n |
|---|---|---|---|---|---|---|
| 20 | (thiazole ring) | H | S | —OEt | 2 | 1 |

TABLE 2

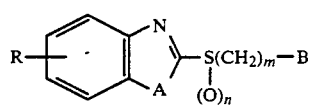

| Example | R | A | B | m | n |
|---|---|---|---|---|---|
| 21 | 5-Cl | S | NHC(=O) NHEt | 2 | 0 |
| 22 | 5-Cl | S | NHC(=O) NHEt | 2 | 1 |
| 23 | 5-Cl | S | NHCH₂CH₂Cl | 2 | 0 |
| 24 | 5-Cl | S | NHCH₂CH₂Cl | 2 | 1 |
| 25 | 5-Cl | S | NHC(=S) NHEt | 2 | 0 |
| 26 | 5-Cl | S | NHC(=NCN) SMe | 2 | 0 |
| 27 | 5-Cl | S | NHC(=NCN) NHEt | 2 | 0 |
| 28 | 5-Cl | S | NHC(=NCN) NHEt | 2 | 1 |
| 29 | 5-Cl | S | NHC(=CHNO₂) SMe | 2 | 0 |
| 30 | 5-Cl | S | NHC(=CHNO₂) NHEt | 2 | 0 |
| 31 | 5-Cl | S | —N(morpholino) | 2 | 0 |
| 32 | 5-Cl | S | —N(morpholino) | 2 | 1 |
| 33 | 5-Cl | S | —N(morpholino) | 2 | 2 |
| 34 | 7-Cl | S | —N(morpholino) | 2 | 0 |
| 35 | 7-Cl | S | —N(morpholino) | 2 | 1 |
| 36 | 6-Cl | S | —N(morpholino) | 2 | 0 |
| 37 | 6-Cl | S | —N(morpholino) | 2 | 1 |
| 38 | 4-Cl | S | —N(morpholino) | 2 | 0 |
| 39 | 4-Cl | S | —N(morpholino) | 2 | 1 |
| 40 | 5-Cl | S | —N(piperidino) | 2 | 0 |
| 41 | 5-Cl | S | —N(piperidino) | 2 | 1 |
| 42 | 5-Cl | S | —N(hexamethyleneimino) | 2 | 0 |
| 43 | 5-Cl | S | —N(hexamethyleneimino) | 2 | 1 |
| 44 | 5-Cl | S | (tetrahydropyran-2-yl) | 1 | 0 |
| 45 | 5-Cl | S | (tetrahydropyran-2-yl) | 1 | 1 |
| 46 | 5-Cl | S | (1-methylpyrrolidin-2-yl) | 2 | 0 |
| 47 | 5-Cl | S | (1-methylpyrrolidin-2-yl) | 2 | 1 |
| 48 | 5-Cl | NH | —N(morpholino) | 2 | 0 |
| 49 | 5-Cl | NH | —N(morpholino) | 2 | 1 |
| 50 | H | NH | —N(morpholino) | 2 | 0 |
| 51 | H | NH | —N(morpholino) | 2 | 1 |

TABLE 2-continued

R—[benzoxazole/thiazole ring]—S(CH₂)ₘ—B with A and (O)ₙ

Structure: $R\text{-}\underset{A}{[\text{ring}]}\text{-S(CH}_2)_m\text{-B}$ with $(O)_n$ on S

| Example | R | A | B | m | n |
|---|---|---|---|---|---|
| 52 | 5-OMe | NH | —N(morpholine) | 2 | 0 |
| 53 | 5-OMe | NH | —N(morpholine) | 2 | 1 |
| 54 | 5-F | S | —N(morpholine) | 2 | 0 |
| 55 | 5-F | S | —N(morpholine) | 2 | 1 |
| 56 | 5-CF₃ | S | —N(morpholine) | 2 | 0 |
| 57 | 5-CF₃ | S | —N(morpholine) | 2 | 1 |
| 58 | 5-NO₂ | S | —N(morpholine) | 2 | 0 |
| 59 | 5-NO₂ | S | —N(morpholine) | 2 | 1 |
| 60 | 7-Cl | S | —OEt | 2 | 0 |
| 61 | 7-Cl | S | —OEt | 2 | 1 |
| 62 | 6-Cl | S | —OEt | 2 | 0 |
| 63 | 6-Cl | S | —OEt | 2 | 1 |
| 64 | 4-Cl | S | —OEt | 2 | 0 |
| 65 | 4-Cl | S | —OEt | 2 | 0 |
| 66 | 5-Cl | S | —OCH₂CH₂Cl | 2 | 0 |
| 67 | 5-Cl | S | —OCH₂CH₂Cl | 2 | 1 |
| 68 | 5-Cl | S | —OCH₂CH₂Cl | 2 | 2 |
| 69 | 5-Cl | NH | —OEt | 2 | 0 |
| 70 | 5-Cl | NH | —OEt | 2 | 1 |
| 71 | 5-OMe | NH | —OEt | 2 | 0 |
| 72 | 5-OMe | NH | —OEt | 2 | 1 |
| 73 | 5-F | S | —OEt | 2 | 0 |
| 74 | 5-F | S | —OEt | 2 | 1 |
| 75 | 5-CF₃ | S | —OEt | 2 | 0 |
| 76 | 5-CF₃ | S | —OEt | 2 | 1 |
| 77 | 5-NO₂ | S | —OEt | 2 | 0 |
| 78 | 5-NO₂ | S | —OEt | 2 | 1 |

The compounds of formula (I) have been found to possess an antiulcer activity.

Water-immersion induced stress ulcer

Wister male rats (11-week age) fasted for 18 hours were placed in a restraint cage, which was in turn immersed to a depth of the pectoral region in water at 20 to 22° C. to leave the rats under stress for six hours. Then, the rats were drawn up from the water and put down by vertebral dislocation. Afterwards, the stomach was removed, infused with 5 ml of a 5% aqueous solution of formalin and was wholly immersed in the same solution for 30 minutes for fixation. The fixed sample was dissected along the curvature ventriculi major, and the ulcer regions were measured along their major length (in mm) by means of slide calipers. The total sum of the measurements per rat is a value of ulcer index.

The compounds under test shown in TABLE 3, suspended in 0.5% carboxymethylcellulose (CMC), were administered to the rats at a single dose of 30 mg/kg body weight of the compound one hour prior to the stressing. To a control group, only 0.5% CMC was administered. The antiulcer activity was calculated according to the following equation:

$$\text{Percent Inhibition of Ulcer} = \left\{1 - \frac{\text{Average value of ulcer index in the test group}}{\text{Average value of ulcer index in the control group}}\right\} \times 100$$

The results are set forth in Table 3.

TABLE 3

| Compound of Example No. | Inhibition (%) |
|---|---|
| 2 | 72.5 |
| 8 | 70.5 |
| 12 | 52.5 |
| 14 | 62.7 |
| 22 | 63.1 |
| 24 | 70.1 |
| 25 | 64.2 |
| 28 | 57.0 |
| 32 | 83.1 |
| 35 | 72.1 |
| 37 | 78.0 |
| 49 | 63.6 |
| 61 | 61.8 |
| 63 | 76.5 |
| 67 | 53.3 |
| 72 | 65.6 |
| 76 | 61.3 |
| 78 | 60.7 |
| Omeprazole | 90.0 |

Ethanol-induced ulcer

Five (5) ml/kg of 100% ethanol was orally administered to Donryu masculine rats fasted for 48 hours and dehydrated for 24 hours. Then, the compounds under test, suspended in 0.5% CMC, were orally administered to the rats at a dose of 5 ml/kg body weight. One hour later, the rats were put down in a similar manner as mentioned above to remove and treat the stomach. A control group, to which only 0.5% CMC was administered, showed a nearly 100% erosion, whereas the compound of Example 32 achieved a 93.0% depression of erosion.

Antimicrobial activity

*Helicobacter pylori* is Gram negative microaerophile which has been recently isolated from human tunica mucosa ventriculi and seems to serve for pathopoiesis and recurrence of ulcer in alimentary canal. The compounds of formula (I) show an antimicrobial activity to inhibit the growth of *Helicobacter pylori*.

The antimicrobial activity was demonstrated using the agar plate dilution method established by the Japan chemotherapy society. The media used were that of Muller-Hinton liquid medium (BBL) containing 7% horse serum, and of Heart-Infusin agar medium (Difco) containing 5% horse defibrinized blood. The culture was incubated for two days at 37° C. using Gaspack (BBL) without a catalyst.

| MINIMUM GROWTH INHIBITION CONCENTRATION (μg/ml) | | |
|---|---|---|
| | Helicobacter p | |
| Compound | HI-0001 | HI-0015 |
| 14 | 50 | 100 |
| 23 | 12.5 | 12.5 |
| 25 | 0.025 | 0.025 |
| 27 | 12.5 | 12.5 |
| 32 | 1.56 | 3.13 |
| 35 | 3.13 | 6.25 |
| 37 | 3.13 | 6.25 |
| 47 | 0.39 | 3.13 |
| 63 | 3.13 | 6.25 |
| 78 | 6.25 | 6.25 |
| Aminobenzylpenicillin | 0.025 | 0.20 |
| Ofloxacin | 0.78 | 0.78 |

Acute Toxicity

When the compound of Example 31 was administered to two groups of mice, three for each group, at a peroral dose of 300 mgkg and an intraperitoneal dose of 100 mgkg, respectively, none of the animals were sacrificed.

What is claimed is:

1. A thiazole derivative having the general formula (I):

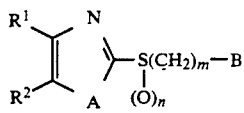

wherein:
R$^1$ and R$^2$ together form a benzene ring which may be optionally substituted by a halogen atom or a lower alkyl optionally substituted by a halogen atom, or lower alkoxy or nitro group;

A represents a sulfur atom;

B represents a lower alkoxy group optionally substituted by a halogen atom; a group —NR$^3$R$^4$ wherein R$^3$ and R$^4$, which may be the same or different, each independently represent a lower alkyl group; or a group —NHC(=Y)R$^5$ where Y represents an oxygen or sulfur atom or a group =NCN or =CHNO$_2$, and R$^5$ represents a group —NHR$^6$ or —SR$^6$ wherein R$^6$ represents a lower alkyl group optionally substituted by a halogen atom;

m represents an integer from 1 to 4; and n represents an integer from 0 to 2;

or a pharmacologically acceptable salt thereof.

2. A compound as claimed in claim 1, wherein B represents the group —NR$^3$R$^4$.

3. A compound as claimed in claim 1, wherein B represents a lower alkoxy group which may be optionally substituted by a halogen atom.

4. A compound as claimed in claim 1, wherein R$^1$ and R$^2$ together form a benzene ring which may be optionally substituted by a halogen atom; and B represents the group —NHC(=Y)R$^5$.

5. A pharmaceutical composition comprising a pharmaceutically effective amount of a compound as claimed in claim 1 together with at least one pharmaceutically acceptable carrier.

6. A method of preventing or treating ulcerative conditions which comprises administering to a mammal an effective amount of a compound as claimed in claim 1.

7. A method as claimed in claim 6, wherein the mammal is a human.

* * * * *